United States Patent
Sakuth et al.

(10) Patent No.: US 6,841,704 B2
(45) Date of Patent: Jan. 11, 2005

(54) PROCESS FOR PREPARING CUMENE WHICH IS USED IN THE PREPARATION OF PHENOL

(75) Inventors: Michael Sakuth, Marl (DE); Uwe Tanger, Bochum (DE); Markus Weber, Haltern (DE)

(73) Assignee: Ineos Phenol GmbH & Co. KG, Gladbeck (DE)

( * ) Notice: Subject to any disclaimer, the term of this patent is extended or adjusted under 35 U.S.C. 154(b) by 27 days.

(21) Appl. No.: 10/204,923

(22) PCT Filed: Feb. 19, 2001

(86) PCT No.: PCT/EP01/01797

§ 371 (c)(1),
(2), (4) Date: Jan. 27, 2003

(87) PCT Pub. No.: WO01/62692

PCT Pub. Date: Aug. 30, 2001

(65) Prior Publication Data

US 2003/0153793 A1 Aug. 14, 2003

(30) Foreign Application Priority Data

Feb. 25, 2000 (DE) .......................................... 100 08 924

(51) Int. Cl.⁷ ............................................... C07L 37/08
(52) U.S. Cl. ........................ 568/798; 585/467; 568/881
(58) Field of Search ................................ 568/798, 881; 585/467

(56) References Cited

U.S. PATENT DOCUMENTS

| | | | | | |
|---|---|---|---|---|---|
| 5,015,786 | A | * | 5/1991 | Araki et al. | 568/798 |
| 5,017,729 | A | * | 5/1991 | Fukuhara et al. | 568/798 |
| 5,160,497 | A | * | 11/1992 | Juguin et al. | 568/798 |
| 5,811,612 | A | * | 9/1998 | Girotti et al. | 585/467 |
| 6,034,291 | A | * | 3/2000 | Girotti et al. | 585/323 |
| 6,084,143 | A | * | 7/2000 | Girotti et al. | 585/467 |
| 6,512,153 | B1 | * | 1/2003 | Cappellazzo et al. | 585/467 |
| 2003/0149314 | A1 | * | 8/2003 | Chewter et al. | 568/955 |

FOREIGN PATENT DOCUMENTS

| | | | |
|---|---|---|---|
| EP | 0371738 | | 6/1990 |
| EP | 000432814 A1 | * | 6/1991 |
| EP | 0538518 | | 4/1993 |
| EP | 000687500 A1 | * | 12/1995 |
| EP | 000847802 A1 | * | 6/1998 |
| EP | 1069100 | | 1/2001 |

* cited by examiner

Primary Examiner—Michael L. Shippen
(74) Attorney, Agent, or Firm—Knobbe, Martens, Olson & Bear, LLP (57) ABSTRACT

Disclosed is a method for the preparation of cumene by reacting isopropanol or a mixture of isopropanol and propene with benzene in the presence of a β-zeolite catalyst having a $SiO_2/Al_2O_3$ molar ratio greater than 10:1 that can be integrated in a process for preparing phenol, which comprises preparing cumene as described above, oxidizing cumene to cumene hydroperoxide, acid-catalyzed cleavage of cumene hydroperoxide to give phenol and acetone, and hydrogenating acetone to form isopropanol.

37 Claims, 4 Drawing Sheets

PROCESS FOR PREPARING CUMENE WHICH IS USED IN THE PREPARATION OF PHENOL

CROSS-REFERENCE TO RELATED APPLICATIONS

This is the U.S. National Phase under 35 U.S.C. § 371 of International Application No. PCT/EPO1/01797, filed Feb. 19, 2001, designating the United States and published in English, which claims priority to German Application No. 100 08 924.0, filed Feb. 25, 2000.

The present invention relates to a process for preparing phenols.

Phenol is an important industrial chemical which is required for the preparation of phenol resins, ε-caprolactam, bisphenol A, adipic acid, alkylphenols, aniline, chlorophenols, picric acid, plasticizers, antioxidants and similar compounds. Phenol is usually prepared from cumene by the Hock process.

In the preparation of phenol from cumene by the Hock phenol synthesis, acetone is formed as a coproduct. Since the commercial demand for phenol is frequently very different from that of acetone, attempts have been made for a long time to find ways of generating downstream products from acetone obtained so as to avoid dependence on the acetone market alone.

A possible downstream product of acetone is isopropanol which can be processed to give ethers such as diisopropyl ether and tert-butyl isopropyl ether.

The conversion of acetone into isopropanol is generally achieved by catalytic hydrogenation. For the production of isopropanol ethers, combination processes involving hydrogenation and etherification are usually employed. Thus, EP 0 694 518, EP 0 665 207, EP 0 652 200 and EP 0 661 257 teach processes for the preparation of various isopropyl ethers. In these patent applications, two process steps frequently proceed in direct succession: namely the catalytic hydrogenation of an acetone-containing, liquid phase and the etherification of the isopropanol obtained in this way over acid catalyst systems. The isopropanol mixture is not worked up after the catalytic hydrogenation.

In addition, EP 0 665 207 teaches a single-stage process in which the hydrogenation and etherification occur in one reactor.

In these processes, which are designed for the preparation of isopropyl ethers, isolation of the isopropanol after hydrogenation of the acetone is very costly because of by-product formation.

Although the preparation of downstream products from acetone enables direct dependence on the acetone market to be avoided, there continues to be a dependence on the market situation for the downstream products. It would therefore be desirable to find a way of producing phenol in which no coproduct is formed.

EP 0 371 738 describes a process for preparing phenol in which the acetone formed in the cleavage of cumene hydroperoxide is hydrogenated to give isopropanol, this isopropanol is used for the alkylation of benzene to give cumene and the cumene is reoxidized to cumene hydroperoxide by means of oxygen. Thus, this process in principle produces phenol from benzene and oxygen. In a preferred embodiment disclosed in EP 0 371 738 a proton-exchanged Y type skeleton zeolite having a ratio of silica to alumina of from 4:1 to less than 10:1 is used in the alkylation step.

In this process, the alkylation of benzene is carried out using isopropanol and/or propene as alkylating reagent in the liquid phase. It has been observed that the yield of alkylation products is decreased by a dehydration reaction of isopropanol which proceeds simultaneously. In addition, the authors have observed an alkylation of benzene by dissolved propene and, on the basis of their observation, only a very low yield of cumene can be achieved. The use of a circulation apparatus in which the olefin-containing stream is continually recycled allows the authors to achieve selective consumption of the isopropanol feed for the alkylation of benzene. This procedure minimizes the proportion of isopropanol which is dehydrated to the olefin and thus is no longer available for the actual alkylation.

The alkylation of benzene to cumene has been examined in more detail in the two Japanese published specifications JP 11-035497 and JP 11-035498. Thus, JP 11-035498 is concerned with the problem of the alkylation of benzene by means of isopropanol producing water which forms an azeotrope with benzene and isopropanol and thus makes the separation of the reaction products difficult. As a solution, it is proposed that the water formed be removed from the reaction mixture prior to separation of unreacted benzene from the reaction mixture. JP 11-035497 is concerned with the problem of the alkylation of benzene by means of isopropanol forming diisopropyl ether which makes the work-up and separation of the reaction products difficult. As a solution, it is proposed that the reaction of benzene and isopropanol be carried out in the presence of water and a zeolite.

U.S. Pat. No. 5,160,497 discloses a phenol production process wherein benzene is reacted with a feedstock comprising propene and isopropanol by contacting a dealuminized Y zeolite with an $SiO_2/Al_2O_3$ molar ratio ranging from 8 to 70. Cumene obtained in this step is oxidized to yield cumyl hydroperoxide, said hydroperoxide is cleaved to obtain a mixture of phenol and acetone and said acetone is hydrogenated to yield isopropanol that is recycled to the alkylation step. Although the examples show that the catalyst is useful for alkylation there is nevertheless the desire to increase conversion and selectivity in respect to cumene in the alkylation step.

In view of the known prior art, it is an object of the present invention to provide a process for preparing cumene by alkylation of benzene with isopropanol, in which, despite dehydration of isopropanol to propene, a more complete conversion of isopropanol, a higher conversion and a higher selectivity in respect of cumene and lower n-propylbenzene formation in the alkylation step, compared to conventional processes, are achieved and which can be easily integrated in a process for preparing phenol comprising the steps I. preparation of cumene by reaction of isopropanol or a mixture of isopropanol and propene with benzene,
II. oxidation of cumene to cumene hydroperoxide,
III. acid-catalyzed cleavage of cumene hydroperoxide to give phenol and acetone and
IV. hydrogenation of acetone to form isopropanol.

This object has been attained by a process for the preparation of cumene by reacting isopropanol or a mixture of isopropanol and propene with benzene in presence of a β-zeolite catalyst having a $SiO_2/Al_2O_3$ molar ratio greater than 10:1.

Another aspect of the present invention is a process for preparing phenol from benzene, which comprises the steps
I. preparation of cumene by reaction of isopropanol or a mixture of isopropanol and propene with benzene,
II. oxidation of cumene to cumene hydroperoxide,
III. acid-catalyzed cleavage of cumene hydroperoxide to give phenol and acetone and IV. hydrogenation of acetone to form isopropanol, wherein, cumene is prepared in accordance with the above described process.

A further aspect of the present invention is a process for the hydrogenation of acetone to isopropanol in at least two process steps, wherein the acetone used is crude acetone.

Sill a further aspect of the present invention is the use of a β-zeolite catalyst having a $SiO_2/Al_2O_3$ molar ratio greater than 10:1 in the alkylation of benzene with isopropanol or a mixture of isopropanol and propene.

It has surprisingly been found that a process for preparing phenol in which cumene is prepared by reaction of isopropanol with benzene over a β-zeolite catalyst having a $SiO_2/Al_2O_3$ molar ratio greater than 10:1, propene is formed by dehydration of isopropanol simultaneously with the alkylation of benzene to cumene by means of isopropanol and the propene formed is likewise used for the alkylation of benzene to cumene makes the preparation of cumene simpler and makes it possible to achieve a more complete conversion of isopropanol and a higher selectivity of the reaction in respect of cumene and reduced formation of n-propylbenzene, so that a higher selectivity can be achieved in the preparation of phenol.

The process of the present invention makes it possible to prepare phenol without the coproduct acetone or downstream products of acetone which do not lead to cumene or isopropanol being formed. The economics of the preparation of phenol is thus only dependent on the achievable sales prices for phenol.

In addition, the process of the invention has the advantage that the dehydration of isopropanol to propene, the alkylation of benzene to cumene by means of the propene formed and the alkylation of benzene to cumene by means of isopropanol can occur simultaneously over β zeolites having $SiO_2:Al_2O_3$ ratios of greater than 10:1 in one synthesis step. The last-named subreactions lead to the desired cumene in higher conversions and with a higher selectivity compared to processes which have been customary hitherto. A further advantage of the process of the invention is that when the reaction is carried out at the same temperature, significantly less n-propylbenzene is formed than in conventional processes. Since n-propylbenzene cannot be used further in an economically feasible way, the avoidance of relatively large amounts of n-propylbenzene allows considerable costs for the reprocessing of this material to be saved. Furthermore, the suppression of the formation of n-propylbenzene increases the selectivity of the reaction in respect of the preparation of cumene.

A further advantage of the process of the invention is that isopropanol which can be used for the alkylation can be prepared by hydrogenation of crude acetone. The ability to hydrogenate crude acetone directly makes it possible to omit complicated work-up or purification of crude acetone obtained, for example, in the cleavage of cumene hydroperoxide. The outlay in terms of apparatus and thus the costs in the overall process for preparing phenol can be further reduced in this way.

The process of the invention for preparing phenol from benzene comprises the four process steps I. preparation of cumene by reaction of isopropanol or a mixture of isopropanol and propene with benzene over an acid catalyst,
II. oxidation of cumene to cumene hydroperoxide,
III. acid-catalyzed cleavage of cumene hydroperoxide to give phenol and acetone and
IV. hydrogenation of acetone to form isopropanol.

The process of the invention is described below by way of example, without being restricted to the description.

A description of the individual processes and process steps which are substeps of the process of the invention will firstly be given.

Step I: Alkylation of Benzene to Cumene by Means of Isopropanol

In this first step, cumene is prepared by reacting isopropanol or a mixture of isopropanol and propene with benzene. The conversion of benzene into cumene is based on an alkylation of benzene by means of an alkylating reagent. Both isopropanol, which is fed into the reactor, and propene, which can be included into the feed stream and/or can be formed in a dehydration reaction which proceeds simultaneously, serve as alkylating reagents. In the process of the invention for preparing cumene by reaction of isopropanol with benzene contacting a β zeolite having a $SiO_2/Al_2O_3$ molar ratio greater than 10:1 as catalyst or the process step according to the invention, propene is formed by dehydration of isopropanol simultaneously with the alkylation of benzene to cumene by means of isopropanol and the propene formed and or included in the feed stream is likewise used for the alkylation. Thus, in principle, three subreactions proceed, preferably simultaneously, in the process of the invention. One reaction is the alkylation of benzene to cumene by means of isopropanol. The second reaction is the dehydration of isopropanol to propene and the third reaction is the alkylation of benzene to cumene by means of the propene.

According to the invention, β zeolites having an $SiO_2:Al_2O_3$ ratio of greater than 10:1 are used as catalyst in the alkylation step. Very particular preference is given to using β zeolite catalysts having an $SiO_2:Al_2O_3$ ratio of from 20:1 to 200:1, preferably greater than 70:1 to 200:1. Due to hydrophobicity of the catalysts resulting from the high modulus, i.e. the high $SiO_2:Al_2O_3$ ratio, the acid centers are not fully occupied by the water formed in the reactions. The actual alkylation reaction, which proceeds simultaneously with the dehydration, is thus not brought to a halt. However, partial occupation of the zeolite surface by the water formed in the reaction achieves a acidity-modifying effect explained in more detail below.

The alkylation reactions and the simultaneous dehydration reaction can be carried out in one or more reactors. The alkylation reactions and the simultaneous dehydration reaction are preferably carried out in a stirred tank reactor, a fixed-bed reactor or a trickle-bed reactor. Moving, suspended or fixed catalysts can be used in the reactor or reactors. Preference is given to using reactors having a fixed catalyst bed charged with suitable shaped bodies, e.g. appropriate extrudates, of the catalyst used.

The starting materials benzene and isopropanol and optionally propene are introduced into the reactor in liquid and/or gaseous form, preferably liquid form. The feed stream to the reactor preferably has a molar ratio of benzene to isopropanol of greater than 1:1, particularly preferably from 3:1 to 10:1. As starting materials fed in, it is possible to use not only pure starting compounds but also compounds containing impurities. The isopropanol used as starting material preferably has a water content of less than 10% by weight, preferably less than 5%.

In the reactor, the reaction of isopropanol with benzene to form cumene, the dehydration reaction which proceeds simultaneously and the reaction of the propene formed or added with benzene to give cumene, i.e. the alkylation reactions, are carried out at a reaction temperature of from 100 to 300° C. The reactor preferably has a temperature gradient which is set so that the reaction mixture in the vicinity of the reactor inlet has a temperature of from 150 to 200° C. and that in the vicinity of the reactor outlet has a temperature of from 250 to 300° C. The reactions are preferably carried out at a pressure of from 10 to 100 bar abs, preferably from 20 to 60 bar abs. Propene is generated in the reactor by the simultaneous isopropanol dehydration. The liquid phase has to be brought into intimate contact with the catalyst so that the alkylation reactions can proceed. This can be ensured, for example when using a trickle-bed reactor, by using high linear velocities of the liquid phases in the reactor, preferably greater than 30 m/h.

The ratio of isopropanol used to benzene and/or the amount of recirculated product influences the water content in the reactor. The water content in turn influences the acidity of the catalyst. If a separate aqueous phase is formed, this has to be intensively dispersed in the reactor. This can be achieved by high linear velocities. The acidity of the catalyst is modified by the water formed in the reaction. According to a preferred embodiment of the present invention the water content of the total feed including optionally recirculated product into the alkylation reactor is maintained to be 5 wt-% at the most. Preferred water contents range from 0.1 to 5 wt-%, more preferred from 0.5 to 4.5 wt-%. This novel measure, which results in an acidity-modified catalyst, makes it possible to minimize the formation of n-propylbenzene, a product of a secondary reaction in the alkylation. The n-propylbenzene content of the reaction mixture or reactor output is usually less than 300 wppm, preferably less than 150 wppm, when carrying out the process of the invention.

The process of the invention for preparing cumene by reaction of isopropanol with benzene in presence of the catalyst of the present invention makes it possible to prepare cumene in one synthesis step. According to the invention, isopropanol is dehydrated to propene in the liquid phase in the presence of the catalyst of the present invention and at the same time benzene is alkylated by means of isopropanol to form cumene. Likewise, the propene formed as an intermediate or that is present in the feed, which can be partly present in a gas phase, reacts simultaneously with the benzene present in the reaction mixture to give the desired cumene. All subreactions are favored or accelerated by the presence of the β zeolite catalyst.

The process of the invention or substeps thereof can be carried out continuously or batchwise. The simultaneous reactions of alkylation and dehydration are preferably carried out continuously. When the process of the invention is carried out batchwise, it has been found that the liquid reaction mixture obtained from the reaction of benzene with isopropanol to form cumene has a propene concentration of less than 1% by weight.

The cumene prepared by the process of the invention can be used directly for the preparation of phenol by the Hock process. However, it can also be advantageous to work up the reaction mixture obtained in the reaction of benzene with isopropanol or to recycle at least part of it to the reactor. The reaction mixture obtained can be worked up by, for example, separating the reaction mixture into organic and aqueous phases, e.g. in a phase separator. The aqueous phase and/or the organic phase can each be further subjected to an extraction. However, the phases obtained can also be passed to a distillation in which the various compounds are removed from the phases. The distillation can be carried out directly using the phases as they are obtained from the reactor or have previously been treated by extraction and/or phase separation.

Preference is given to separating the reaction mixture obtained from the reactor into an organic phase and an aqueous phase in a liquid/liquid phase separator like a decanter prior to distillation, in which case it can be advantageous to remove part of the heat energy from the reaction mixture before it enters the phase separator, e.g. by means of a heat exchanger. This embodiment is advantageous in that water is removed from the reactor effluent prior to distillation thereby reducing energy consumption. Additionally by applying this measure the water content of the recirculated portion of the reactor effluent can be easily controlled to adjust the water content of the total feed stream into the alkylation reactor.

The aqueous phase can be worked up or disposed of. The work-up of the aqueous phase can comprise, for example, transferring the aqueous phase to a distillation apparatus in which an IPA-water azeotrope is separated from the remaining aqueous phase. The water-IPA azeotrope can be returned to the alkylation reactor.

The organic phase is fed to a distillation column in which cumene, by-products and starting materials are separated from one another. The starting materials which have been separated off can be returned to the reactor. It can be advantageous to return part of the organic phase and/or part of the aqueous phase of the reaction mixture without work-up to the reactor. The organic phase of the reaction mixture is preferably returned to the reactor in such an amount that the ratio of the recycled organic part of the reaction mixture to starting materials is from 1:1 to 100:1. It may be advantageous to remove part of the heat energy from the organic part of the reaction mixture which is recycled to the reactor by means of a heat exchanger. The recycle of the organic part of the reaction mixture can be achieved, for example, by means of a circulation line in which a pump is installed. The circulation line is preferably provided with a heat exchanger by means of which it is possible to influence the temperature of the organic part of the reaction mixture. The temperature of the recycled, organic part of the reaction mixture is preferably set so that the temperature of the mixture of recycled reaction mixture and starting materials corresponds approximately to the temperature at the reactor inlet.

The cumene separated off in the distillation column can be passed to work-up or further use in the Hock phenol process, e.g. the oxidation. The by-products which have been separated off, for example polyisopropylbenzene or diisopropylbenzene, can be passed to further utilization or work-up. Such work-up steps can include, for example, transalkylation reactions in which the by-products can in large part be converted into cumene. The method of carrying out such transalkylation reactions is known to those skilled in the art.

Step II: Oxidation of Cumene to Cumene Hydroperoxide

The oxidation of cumene to cumene hydroperoxide can be carried out in a manner known to those skilled in the art. For example, the oxidation can be carried out as described in EP 0 371 738. The oxidation of cumene is usually carried out at a temperature of from 60 to 150° C., preferably at a temperature of from 90 to 130° C. The oxidation of cumene is preferably carried out at a pressure of from 1 to 10 kg/cm$^2$. The oxidation is carried out using molecular oxygen. This molecular oxygen can be supplied in the form of oxygen gas, air or a mixture of oxygen gas or air with an inert gas, e.g. nitrogen or a noble gas.

The gas comprising molecular oxygen is brought into contact with the cumene in the form of a cumene-containing solution. The contact between oxygen-containing gas and the cumene should be very intimate. This can be achieved in a manner known to those skilled in the art, e.g. by means of a bubble column reactor.

The cumene-containing solution preferably has a pH of greater than 2. The pH of the cumene-containing solution can be adjusted by addition of alkaline compounds to this solution. The pH of the cumene-containing solution can also be adjusted by work-up of the cumene used, e.g. by extraction of acidic constituents. As alkaline compounds, preference is given to adding aqueous solutions of sodium or potassium carbonate or hydroxide. The addition of the alkaline compound to the cumene-containing solution is preferably carried out so that the pH of the cumene-containing solution does not go outside the pH range from 2 to 11 even as the reaction progresses.

An agent which initiates the oxidation reaction is preferably added to the reaction system. As initiators for the oxidation reaction, an azo compound such as α,α'-azobisisobutyronitrile or α,α'-azobis(cyclohexyl nitrile) can advantageously be added to the reaction system. However, cumene hydroperoxide can also be advantageously added as initiator to the reaction system. This has the advantage that no additional extraneous compounds are introduced into the reaction system. Preference is given to adding from 0.01 to 20% by weight of the initiator, based on the total weight of the starting materials, to the reaction system.

The oxidation of the cumene can be carried out continuously, batchwise or semicontinuously. The oxidation of the cumene to cumene hydroperoxide is preferably carried out continuously.

It can be advantageous for the reaction mixture obtained in the oxidation to be subjected to an after-treatment. The reaction mixture obtained in the oxidation is preferably concentrated so as to give a solution containing from 40 to 90% by weight of CHP, particularly preferably from 60 to 85% by weight of CHP. Concentration is preferably carried out by distillation of unreacted cumene from the reaction mixture.

Step III: Acid-Catalyzed Cleavage of Cumene Hydroperoxide into Phenol and Acetone The process step of acid-catalyzed cleavage of cumene hydroperoxide can be carried out in a manner known to those skilled in the art. The acid-catalyzed cleavage of cumene hydroperoxide is described, for example, in EP 0 589 588, U.S. Pat. No. 4,016,213, DP 1 443 329, U.S. Pat. No. 4,358,618, GB 930 161 or EP 0 371 738.

The acid-catalyzed cleavage of cumene hydroperoxide (CHP) can be carried out homogeneously or heterogeneously. The cleavage of CHP is preferably carried out by homogeneous cleavage. As catalysts, it is possible to use strong acids such as sulfuric, hydrochloric or hydrofluoric acid. It is likewise possible to use heteropolyacids. It is also possible to use solid catalysts, e.g. acidic ion exchange resins or acidic zeolites. If liquid acids are used, they are added to the reaction mixture comprising CHP. Preference is given to adding an acid catalyst to the reaction mixture in such an amount that the content of acid catalyst is from 0.002 to 5% by weight.

The reaction mixture usually comprises not only CHP but also a solvent. Solvents which can be used are aromatic or aliphatic hydrocarbons, e.g. cumene, benzene, hexane, heptane or cyclohexane, alcohols such as ethanol, methanol, propanol or isopropanol, or ketones or aldehydes, e.g. acetaldehyde, acetone, methyl isobutyl ketone. Preference is given to using phenol, cumene and/or acetone as solvent. The solvent content of the reaction mixture in the cleavage reactor is from 1 to 25 times the CHP content.

The actual cleavage is preferably carried out in one or more reactors. The temperature in this reactor or these reactors is preferably from 40 to 90° C. The reaction mixture which is taken from the reactor or reactors can be recirculated at least partly to the reactor inlet. Preference is given to recirculating at least 25–95% of the reaction mixture taken from the reactor outlet to the inlet of the cleavage reactor or reactors.

It may be advantageous to carry out a subsequent heat treatment subsequent to the actual cleavage. For this purpose, the reaction mixture obtained from the cleavage reactor is transferred to a tube reactor. The tube reactor is preferably at a temperature of from 80 to 100° C. The intention of the subsequent heat treatment is to cleave both CHP which has not been cleaved in the cleavage reactors and dicumyl peroxide (DCP) which may have been formed from CHP and dimethylbenzyl alcohol in the cleavage reactors.

The cleavage product mixture, which can come directly from the cleavage reactor or else from the subsequent heat treatment, is worked up by distillation. This work-up produces, in a first separation step, crude acetone which can be hydrogenated to give isopropanol. In further distillation steps, the desired phenol is isolated from the cleavage product mixture and can be passed to work-up or use. Unreacted cumene and compounds which may have been formed by secondary reactions, e.g. AMS, can be recycled to the overall process in a manner known to those skilled in the art.

Step IV: Hydrogenation of Acetone to Isopropanol

The process of the invention or the process step according to the invention makes it possible to prepare isopropanol from acetone containing impurities, by hydrogenation of acetone. In particular, the process of the invention makes it possible to prepare isopropanol from crude acetone, e.g. crude acetone which is obtained in the acid-catalyzed cleavage of cumene hydroperoxide.

Typical impurities in crude acetone are, for example, water, cumene and/or acetaldehyde. Crude acetone containing up to 15% by weight of impurities can be used in the process or process step according to the invention. Preference is given to using crude acetone containing from 2.5 to 13% by weight of impurities. Crude acetone to be used according to the invention can contain up to 5% by weight of water, 7.5% by weight of cumene and/or 3 000 wppm of acetaldehyde.

The hydrogenation not only converts acetone into isopropanol but also converts the cumene into hydrocumene and the acetaldehyde into ethanol. Depending on the purpose for which the isopropanol prepared according to the invention is to be used, these compounds can be separated from the isopropanol in a manner known to those skilled in the art.

The process of the invention or the process step according to the invention can be carried out in one or more stages. The process of the invention is preferably carried out in at least two stages. The process stages can be carried out individually, in parallel and/or in a cascaded manner. The process stages are preferably carried out in a circuit or tube reactor.

The hydrogenation of acetone is preferably carried out as a liquid-phase hydrogenation. The liquid-phase hydrogenation is preferably carried out at a temperature of from 60 to 140° C., more preferably from 70 to 130° C., and a pressure of from 10 to 50 bar, more preferably from 20 to 35 bar. In the various process stages, different temperature and/or pressure conditions can be employed.

The hydrogenation can be carried out using equimolar amounts of hydrogen and acetone. The hydrogenation is preferably carried out using an excess of hydrogen. The molar ratio of hydrogen to acetone is preferably at least 1:1.

The hydrogenation is preferably carried out at a feed ratio of hydrogen to acetone of from 1:1 to 5:1, particularly preferably from 1:1 to 1.5:1.

Apart from the hydrogenation reactions, it is possible for further reactions in which acetone and/or isopropanol is consumed to occur, e.g. catalyzed by a catalyst. For example, alkali-catalyzed aldol condensation of acetone can form diacetone alcohol (DAA) which can be hydrogenated to hexylene glycol (HG). Elimination of water from DAA and hydrogenation of the mesityl oxide (MOX) formed by elimination of water can produce methyl isobutyl ketone (MIBK) which can be hydrogenated to give 4-methyl-2-pentanol (MPOL). The desired product isopropanol can react further by elimination of water to form diisopropyl ether (DIPE).

Since the occurrence of these secondary reactions decreases the yield of isopropanol based on the acetone used, the catalyst used should not promote these reactions. For this reason, a catalyst should ideally be neutral, i.e. not alkaline and not acidic.

Suitable catalysts for carrying out the process of the invention are commercial hydrogenation catalysts comprising Cu, Cr, Ru and/or Ni as active component on neutral support materials such as $Al_2O_3$, $TiO_2$, $SiO_2$, activated carbon and/or $ZrO_2$, or support materials comprising mixtures thereof. Particular preference is given to using nickel-containing catalysts comprising about 10% by weight of nickel on a neutral support. Suitable neutral support materials are, in particular, alpha-$Al_2O_3$, $TiO_2$, $ZrO_2$ and mullite.

The process of the invention is preferably carried out in at least two process stages, where the reactor of the 1st process stage is configured as a circulation reactor and the reactor of the 2nd process stage is configured as a tube reactor.

A major part of the conversion of acetone occurs in the circulation reactor. The circulation reactor is equipped with a product recycle loop. The reactor preferably works at a high concentration level and can therefore be operated using a small circulation ratio. The ratio of circulated product stream to acetone fed in is from 0.5:1 to 20:1, preferably from 2:1 to 10:1. It can be advantageous to cool the reaction product from the circulation reactor. It is possible to cool both the substream of the reaction product which is recirculated to the reactor and also the substream which is passed to the 2nd process stage or the tube reactor.

The initial temperature of the 1st process stage is advantageously from 60 to 90° C., and the total pressure is from 10 to 50 bar. Depending on the initial activity of the catalyst, it may be advantageous to reduce the initial temperature or to increase the circulation ratio in order to set the desired outlet temperature, which may correspond to the inlet temperature of the tube reactor.

Since the hydrogenation is an exothermic reaction, the temperature increases in the reactor, so that cooling may be provided in and/or downstream of the circulation reactor. The hydrogenation in the first process stage is preferably carried out at a temperature of from 60 to 140° C., preferably from 70 to 130° C., and a pressure of from 10 to 50 bar, preferably from 20 to 35 bar.

To hydrogenate acetone which has not been reacted in the first process stage, the reaction mixture from the circulation reactor is passed to a tube reactor. Such a tube reactor can be, for example, a shaft reactor operated as a tube reactor.

The 2nd process stage, which preferably has plug flow characteristics, is preferably carried out at a temperature of from 60 to 140° C., preferably from 70 to 130° C., and a pressure of from 20 to 50 bar.

The above-described catalysts or catalyst systems comprising catalyst and catalyst support can be used in both process stages. Preference is given to using a nickel-containing catalyst comprising about 10% by weight of nickel on a neutral support in both process stages.

Combining the process steps I to IV of the process of the invention makes it possible to prepare phenol from benzene and oxygen without obtaining the coproduct acetone. Thus, for example, it may be advantageous for the acetone formed in the cleavage of CHP in process step III of the process of the invention to be used at least partly in step IV in the hydrogenation of acetone to isopropanol as starting material. Since crude acetone can be used directly as starting material for the hydrogenation in process step IV of the process of the invention, costly work-up of the crude acetone, as is required in conventional processes, can be omitted. It is naturally also possible to use purified and/or purchased acetone in the hydrogenation. The isopropanol formed in the hydrogenation of the acetone or crude acetone can be used directly for the alkylation of benzene (process step I). However, it can likewise be advantageous for the isopropanol from step IV to be purified by suitable measures, e.g. a thermal work-up, before use in the alkylation. The thermal work-up can, for example, comprise purification of the isopropanol by distillation in two distillation columns, with low boilers being separated off in the first column and high boilers being separated off in the second column.

A person skilled in the art of phenol production will be able to see further possible combinations which are likewise subject matter of the present invention. Thus, it is possible to combine individual process steps according to the invention with other advantageous process steps. Such combinations are also subject matter of the present invention.

Figure 1:
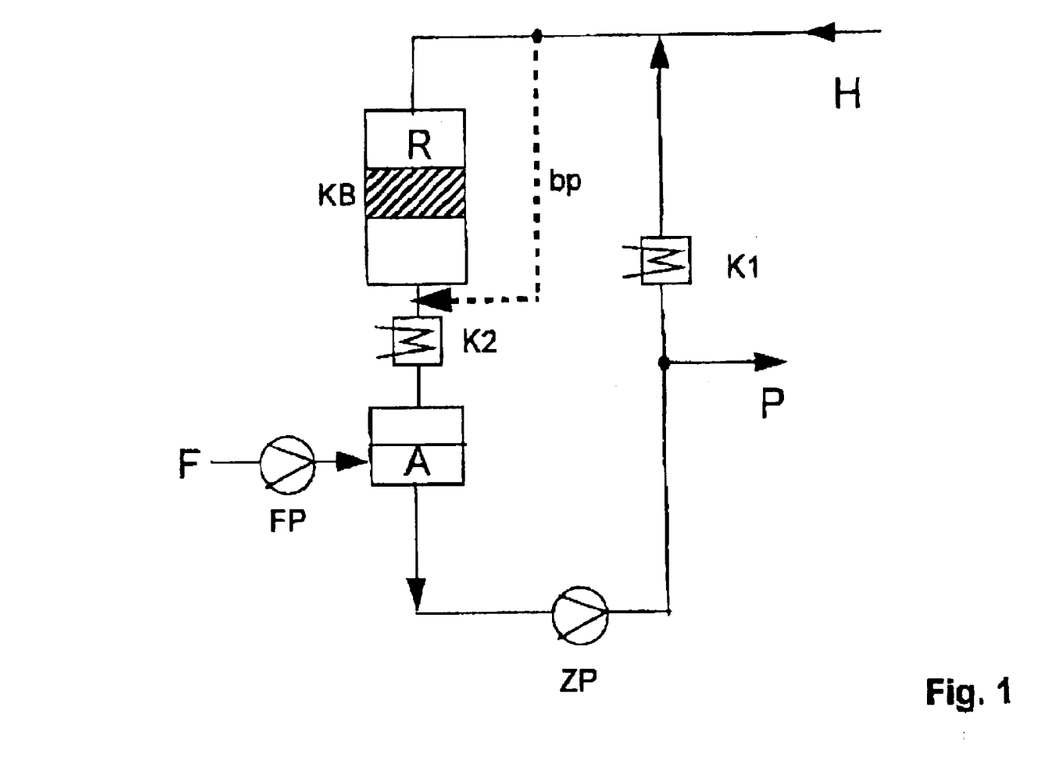
FIG. 1 and FIG. 2 show two embodiments of the substep of the process of the invention in which isopropanol is prepared from crude acetone by hydrogenation.

FIG. 1 shows one embodiment of the process step of acetone hydrogenation in the process of the invention, without the process being restricted to this embodiment.

The feed F can be placed in the separation vessel A by means of the pump FP or can be fed in continuously in the case of continuous operation. From the separation vessel, the reaction mixture can be circulated by means of the circulation pump ZP either via the bypass bp or the reactor R in which the catalyst bed KB is located. The reaction mixture can be heated to the desired temperature by means of the heat exchanger K1. Hydrogen is introduced into the system via H. The reactor R is followed by a cooler K2 in which the reaction mixture can be cooled. After cooling, the reaction mixture goes to the phase separation vessel A. Product can be taken from the reaction system via P.

Figure 2:
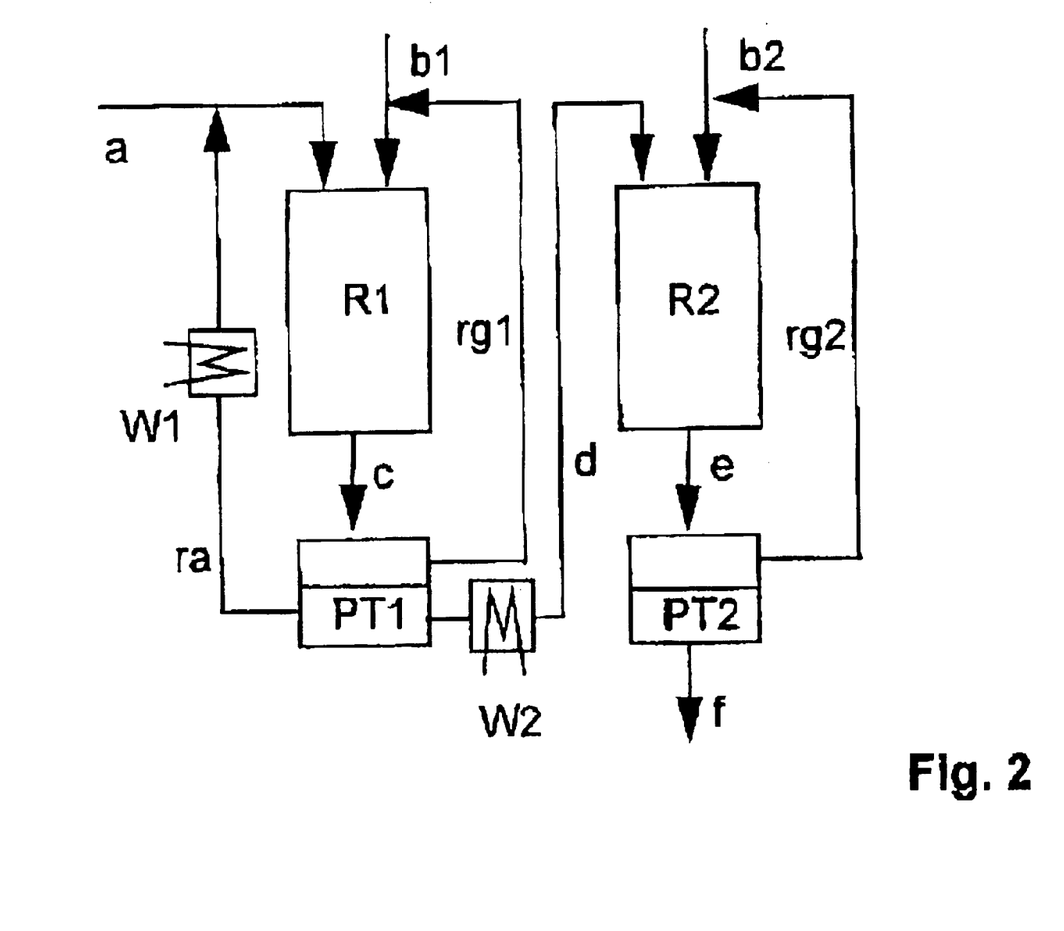

FIG. 2 shows a further embodiment of the process step of acetone hydrogenation in the process of the invention, without the process being restricted to this embodiment.

In this embodiment, a crude acetone stream a together with a hydrogen stream b1 is fed into a circulation reactor R1. The reaction mixture is conveyed from the circulation reactor via line c to a phase separation apparatus PT1. Unconsumed hydrogen is separated from the reaction mixture formed in the circulation reactor by phase separation in the phase separator PT1. This hydrogen can be fed back into the circulation reactor via line rg1. The liquid part of the reaction mixture can likewise be recirculated at least partly to the circulation reactor via line ra. Heat can be introduced into or removed from the recirculated reaction mixture by means of the heat exchanger W1. Part of the liquid part of the reaction mixture can be conveyed via line d to a tube reactor R2, with the reaction mixture being brought to a particular temperature in a heat exchanger W2. The reaction mixture is conveyed together with hydrogen from line b2 to the tube reactor R2. The reaction mixture leaves the tube reactor via line e. After leaving the tube reactor via line e, hydrogen present in the reaction mixture is again separated from the liquid part of the reaction mixture by phase separation (e.g. by flashing off) in the phase separation apparatus PT2 and can be fed back into the tube reactor via line rg2. Via line f, the isopropanol formed by the hydrogenation of crude acetone is passed to further use.

Figure 3:
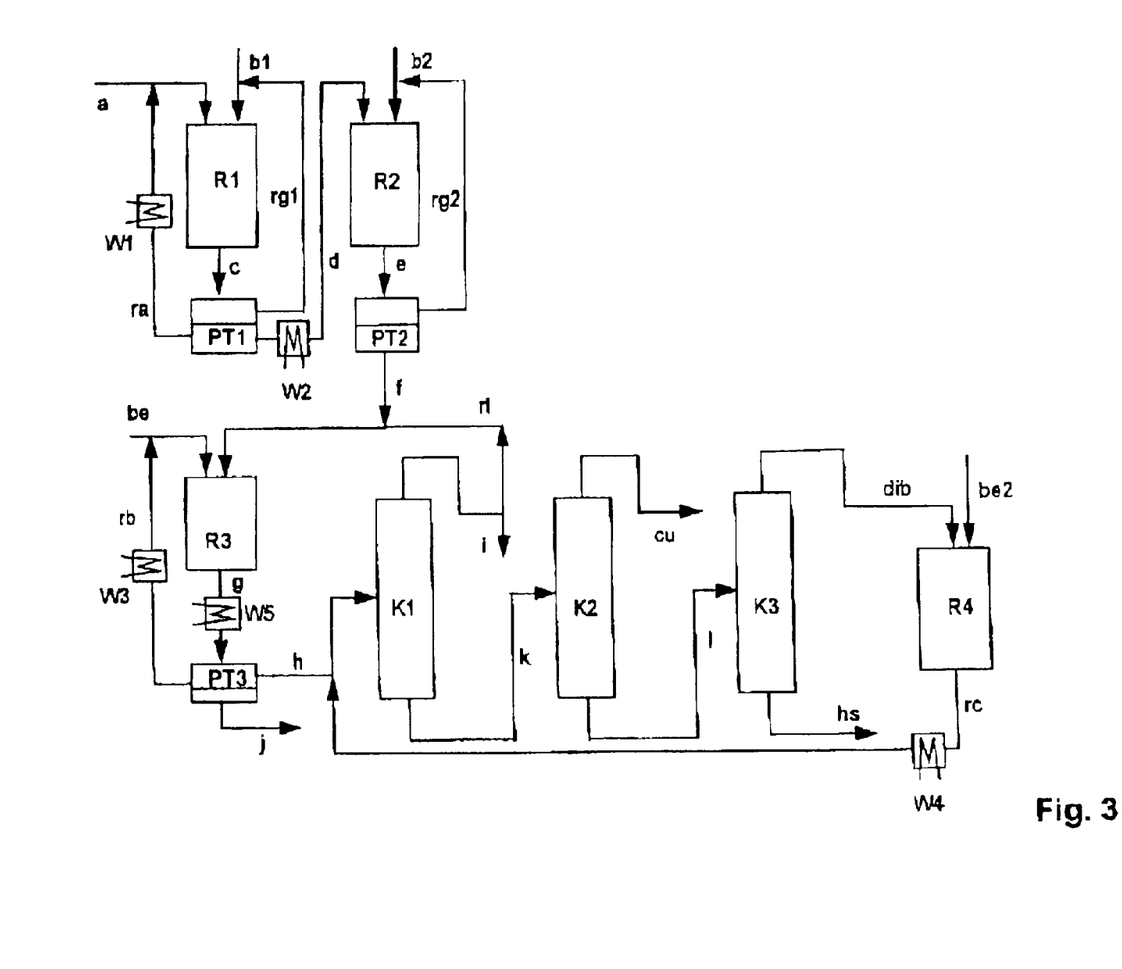
FIG. 3 and FIG. 4 show two embodiments of the overall process in which cumene is obtained from acetone and benzene.

FIG. 3 shows one embodiment of the process of the invention, without the process being restricted thereto.

In this embodiment of the process of the invention, a crude acetone stream a obtained in the cleavage of CHP is hydrogenated in a process step as described for FIG. 2 to form isopropanol which is obtained via line f. This is used for the alkylation of benzene to cumene.

For this purpose, the liquid phase from line f is fed into the reactor R3. Benzene is also fed into this reactor via line be. The alkylation takes place in this reactor. The reaction mixture from reactor R3 is transferred via line g and the heat exchanger W5 to the phase separation apparatus PT3. From this, an aqueous phase can be conveyed via line j to a work-up step for the recovery of products of value, e.g. cumene or isopropanol dissolved in water, or to disposal. Via line rb, part of the organic phase of the reaction mixture can be recirculated to the reactor R3. Heat can be removed from or introduced into this recycled part of the reaction mixture by means of the heat exchanger W3. Part of the organic phase of the reaction mixture is conveyed via line h to the distillation column K1. At the top of the column, a product comprising predominantly benzene and/or isopropanol is taken off. Part of this can be fed back into the reactor R3 via line ri or part of it can be removed from the system via line i and passed to another use or work-up. At the bottom of the column K1, a mixture boiling at a higher temperature than isopropanol is taken off and can be fed via line k into the side of the distillation column K2. At the top of the column K2, a cumene-containing fraction is taken off and this can be conveyed via line cu to further work-up or use, e.g. the oxidation. A fraction having a boiling point higher than that of cumene is obtained at the bottom of this column K2. This fraction can be fed via line l to the distillation column K3. In the column K3, polyisopropylbenzenes and/or diisopropylbenzenes are separated from high boilers. The multiply alkylated benzenes are taken off at the top of the column and conveyed via line dib to the reactor R4. High boilers are obtained at the bottom of the column K3 and can be passed via line hs to work-up or use. In addition to the multiply alkylated benzenes, benzene is introduced via line be2 into the reactor R4 in which the transalkylation takes place. The reaction mixture leaving the reactor is fed via line re, in which the heat exchanger W4 by means of which heat can be removed from or introduced into the reaction mixture is located, into the distillation column K1.

Figure 4:
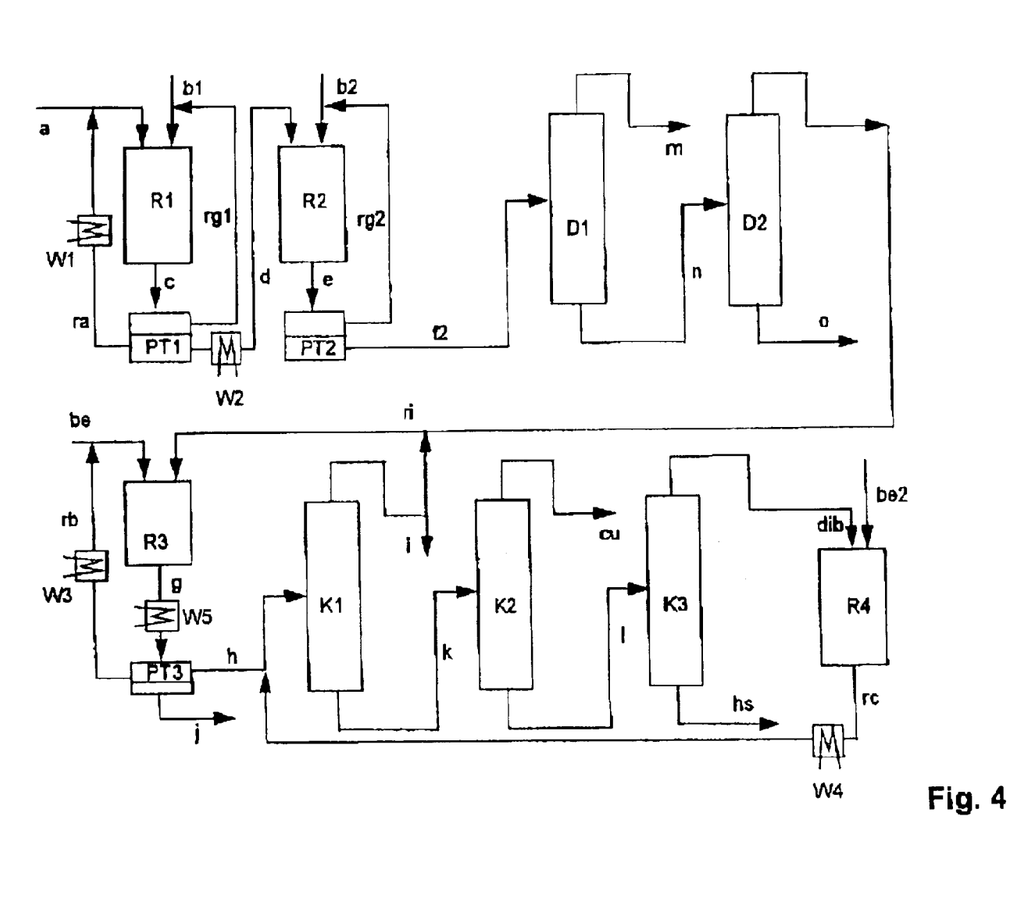

FIG. 4 shows a further embodiment of the process of the invention, without the process being restricted thereto.

In this embodiment of the process of the invention, the isopropanol is not, as shown in FIG. 3, fed directly to the alkylation but instead is firstly worked up and purified by distillation and subsequently fed to the alkylation reactor. Unlike the embodiment shown in FIG. 3, the reaction mixture obtained in the phase separation apparatus PT2 or the liquid part of the reaction mixture is not conveyed directly to the reactor R3, but is instead conveyed via line f2 to the distillation column D1. In this, the isopropanol is separated from low boilers. These low boilers, e.g. acetone, are taken off at the top of the column via line m and are passed to work-up. If the low boilers are mainly made up of acetone, this can be fed back into the reactor R1. The fraction taken off at the bottom of the column can be conveyed via line n to a further distillation column D2. In this distillation column, isopropanol is separated from high boilers. The isopropanol taken off at the top of the column can be passed via line ri to the reactor R3 in which the alkylation reaction takes place as in FIG. 3. The high boilers separated off from the isopropanol and obtained at the bottom of the column can be passed via line o to work-up or use.

EXAMPLE 1

Hydrogenation of Acetone (Batchwise Procedure)

In an experimental plant as shown in FIG. 1, the circulation reactor was charged with about 65 g of catalyst (10% nickel on α-aluminium oxide). The feed F is placed in the separation vessel A and circulated by pumping via the bypass bp. The apparatus is subsequently brought to the desired temperature. At the beginning of the reaction, the reactor R is switched to the circuit. After about 5 minutes, a constant temperature and a constant pressure have been established, and the first product samples are taken. The temperature was about 130° C. and the pressure was 25 bar abs (partial pressure of $H_2$: about 20 bar abs). Hydrogen was introduced via line H. Hydrogen was introduced automatically in an amount corresponding to that consumed by the hydrogenation. As feed, acetone containing the impurities shown in table 1 was initially placed in the separation vessel A. Table 1 likewise indicates the composition of the reaction mixture after the hydrogenation.

TABLE 1

Composition of the reaction mixture from example 1 before and after hydrogenation (DL = detection limit)

| Amounts in % by mass | Before hydrogenation | After hydrogenation |
|---|---|---|
| Water | 3.9 | 38 |
| Acetone | 94.3 | 0.08 |
| Methanol | 0.019 | 0.011 |
| Isopropanol | <DL | 95.0 |
| Diacetone alcohol | <DL | 0.023 |
| 2-Methyl-2,4-pentanediol | <DL | 0.039 |
| Acetaldehyde | 0.09 | <DL |
| Dimethoxymethane | <DL | 0.001 |
| Cumene | 1.6 | 0.013 |
| Hydrocumene | 0.002 | 0.9 |

As can be seen from the table, the process step according to the invention is very suitable for preparing isopropanol from crude acetone.

EXAMPLE 2

Hydrogenation of Acetone to Isopropanol which is Subsequently Used for the Alkylation of Benzene to Cumene In a plant as described in FIG. 4, crude acetone comprising 94% by weight of acetone together with water (about 4% by weight) and cumene (about 1.2% by weight) and also, at least, methanol, acetaldehyde, dimethoxymethane, hydrocumene, diacetone alcohol and 2-methyl-2,4- pentanediol in amounts of about 100 wppm each is fed into the circulation reactor which is provided with a reduced and stabilized nickel catalyst (10% nickel on α-aluminium oxide). In addition, a stream of hydrogen is fed into the circulation reactor. The circulation ratio was 2.5:1. The hydrogenation of the crude acetone in the circulation reactor is carried out at a temperature of from 60 to 140° C. and a pressure of from 20 to 40 bar abs.

The reaction mixture taken from the circulation reactor was depressurized to separate off the hydrogen and was subsequently conveyed to a tube reactor into which hydrogen gas was likewise fed and which was likewise provided with a reduced and stabilized nickel catalyst. The after-hydrogenation of crude acetone which had not been hydrogenated in the circulation reactor occurred in this tube reactor which had a temperature profile of from 90 to 132° C. and a pressure of from 20 to 40 bar abs. After separating off the hydrogen, the reaction mixture had the following composition: about 94% by weight of isopropanol, 0.5% by weight of acetone, 4% by weight of water, about 1.2% by weight of hydrocumene together with dimethoxymethane, methyl isobutyl ketone, diacetone alcohol, hexylene glycol, 4-methyl-2-pentanol and 2-methyl-2,4-pentanediol in the low wppm range. Cumene and acetaldehyde could no longer be detected in this mixture.

This reaction mixture was worked up by introducing it into a first distillation column in which the low boilers, e.g. acetone, methanol and dimethoxymethane, were separated from the reaction mixture at the top. The remaining reaction mixture was taken from the bottom of this column and fed into a further distillation column. In this distillation column, the isopropanol was separated from the reaction mixture and taken off at the top of the distillation column.

The isopropanol obtained in this way was fed directly into a circulation reactor into which benzene was also fed. The alkylation took place in this circulation reactor at a pressure of about 45 bar abs, and the reactor had a temperature profile of from 200 to 230° C. In a downstream phase separation vessel, the reaction mixture was separated into an organic phase and an aqueous phase. The aqueous phase, which is saturated with organic constituents, was distilled and the water-isopropanol azeotrope which was distilled off was recirculated to the circulation reactor. The organic phase from the phase separation vessel was partly recirculated to the circulation reactor, with the circulation ratio of recycled organic parts of the reaction mixture to starting materials fed into the reactor being 5:1. The other part of the organic phase of the reaction mixture was passed to three distillation columns connected in series. In the first distillation column, low boilers such as propene, benzene and unreacted isopropanol were separated off from the organic phase. These low boilers were fed back into the circulation reactor as alkylation reagent. The bottoms from this column were passed to the next column in which cumene was separated from the remaining organic phase. This cumene was fed directly to the oxidation for preparing cumene hydroperoxide (CHP). The bottoms from the distillation column were fed into the third distillation column in which diisopropylbenzene and/or polyisopropylbenzenes were separated from the remaining organic, high-boiling compounds. The bottoms were passed to thermal utilization. The multiply alkylated benzenes were conveyed to a tube reactor into which benzene was also fed. A transalkylation reaction was carried out at a temperature of about 220° C. and a pressure of 40 bar abs in the presence of zeolites as catalyst to form cumene from benzene and multiply alkylated benzenes. The reaction mixture from this reactor was conveyed back to the first distillation column after the alkylation reactor so as to be able to separate unreacted benzene from the reaction mixture once again, then to separate the cumene from the reaction mixture in the next distillation column and to feed it to the oxidation.

EXAMPLE 3

Alkylation of Benzene with Isopropanol
(Discontinuously)

In a stirred tank reactor 881 g (85 wt-%) benzene was reacted for one hour with 156 g (15 wt-%) isopropanol in presence of 8 g of the catalyst shown in table 2 at a temperature of 230° C. and a pressure of 50 bar abs. The composition of the reaction product was analyzed by gas chromatography after termination of the reaction. The results are given in table 2.

TABLE 2

Composition of the reaction product of example 3

| | Catalyst | |
| --- | --- | --- |
| | H-β-150 (β-Zeolith) | H-DAY-55 (Y-Zeolith)* |
| cumene | 22.6 wt.-% | 13.6 wt.-% |
| diisopropylbenzene | 2.3 wt.-% | 1,8 wt.-% |
| triisopropylbenzene | 0.0 wt.-% | 0.1 wt.-% |
| diisopropylether | 0.06 wt.-% | 0.06 wt.-% |
| cumene selectivity in respect of benzene | 93.1% | 90.6% |
| cumene selectivity in respect of isopropanol | 71.2% | 42.4% |
| benzene conversion | 17.4% | 9.9% |

*prior art catalyst

Example 3 demonstrates, that by using the catalyst according to the present invention in the alkylation step an improved cumene selectivity as well as an increased benzene conversion compared with the prior art catalyst could be achieved.

What is claimed is:

1. A method for the preparation of cumene comprising reacting isopropanol or a mixture of isopropanol and propene with benzene in presence of a β-zeolite catalyst having a $SiO_2/Al_2O_3$ molar ratio greater than 10:1, wherein the acidity of the catalyst is modified by surface addition of water, and wherein the isopropanol used is obtained by hydrogenation of acetone in at least two process stages.

2. The method of claim 1, wherein the catalyst used is a β-zeolite having an $SiO_2:Al_2O_3$ ratio of from 20:1 to 200:1.

3. The method of claim 1, wherein the reacting occurs in a reactor that receives a feed stream, and wherein the water content of the total feed stream to the reactor does not exceed 5 wt.-% based on the weight of the total feed stream.

4. The method of claim 3, wherein the water content ranges from 0.1 to 5 wt.-%.

5. The method of claim 1, wherein the reacting occurs in a reactor that receives a feed stream, and wherein the molar ratio of benzene to isopropanol in the feed stream to the reactor is greater than 1:1.

6. The method of claim 5, wherein the molar ratio of benzene to isopropanol in the feed stream to the reactor for the reaction of benzene with isopropanol is from 3:1 to 10:1.

7. The method of claim 1, wherein the reaction is carried out at a temperature of from 100 to 300° C.

8. The method of claim 1, wherein the reaction is carried out at a pressure of from 10 to 100 bar abs.

9. The method of claim 1, wherein the reaction is carried out in a stirred tank reactor, a trickle-bed reactor or a fixed-bed reactor.

10. The method of any claim 1, wherein the reacting occurs in a reactor that receives a feed stream, and wherein the reaction mixture is, after leaving the reactor, separated into an aqueous phase and an organic phase by liquid/liquid phase separation.

11. The method of claim 10, wherein part of the organic phase of the reaction mixture is returned to the reactor.

12. The method of claim 11, wherein the ratio of the recycled organic phase of the reaction mixture to starting materials is from 2:1 to 100:1.

13. The method of claim 1, wherein the reaction mixture has an n-propylbenzene concentration of less than 300 wppm.

14. A method for preparing phenol from benzene, comprising:

preparing cumene, comprising reacting isopropanol or a mixture of isopropanol and propene with benzene in presence of a β-zeolite catalyst having a $SiO_2/Al_2O_3$ molar ratio greater than 10:1, wherein the acidity of the catalyst is modified by surface addition of water, oxidizing cumene to cumene hydroperoxide, performing an acid-catalyzed cleavage of cumene hydroperoxide to give phenol and acetone; and hydrogenating acetone to form isopropanol, wherein the isopropanol used is obtained by hydrogenation of acetone in at least two process stages.

15. The method of claim 14, wherein the acetone used is crude acetone.

16. A method for the hydrogenation of acetone to isopropanol, wherein said hydrogenation of acetone to isopropanol comprises at least two process stages, and wherein the acetone used is crude acetone.

17. The method of claim 14, wherein the hydrogenation is carried out as a liquid-phase hydrogenation at a temperature of from 60 to 140° C. and a pressure of from 20 to 50 bar.

18. The method of claim 15, wherein the crude acetone contains up to 15% by weight of impurities.

19. The method of claim 18, wherein the crude acetone contains from 2.5 to 13% by weight of impurities.

20. The method of claim 18, wherein the crude acetone contains up to 5% by weight of water.

21. The method of claim 18, wherein the crude acetone contains up to 7.5% by weight of cumene.

22. The method of claim 18, wherein the crude acetone contains up to 3000 wppm of acetaldehyde.

23. The method of claim 14, wherein the acetone conversion in the hydrogenation is at least 99%.

24. The method of claim 14, wherein a catalyst comprising Ni, Cu, Ru, Cr or a mixture thereof on a neutral support is used for the hydrogenation.

25. The method of claim 24, wherein a nickel-containing catalyst on an $\alpha$-$Al_2O_3$ support is used.

26. The method of claim 4, wherein the water content ranges from 0.5 to 4.5 wt.-%.

27. The method of claim 1, wherein the reaction mixture has an n-propylbenxene concentration of less than 150 wppm.

28. The method of claim 20, wherein the crude acetone contains up to 7.5% weight of cumene.

29. The method of claim 19, wherein the crude acetone contains up to 3000 wppm of acetaldehyde.

30. The method of claim 18, wherein the acetone conversion in the hydrogenation is at least 99%.

31. The method in claim 30, wherein the acetone conversion in the hydrogenation is at least 99%.

32. The method of claim 18, wherein a catalyst comprising Ni, Cu, Ru, Cr or a mixture thereof on a neutral support is used for the hydrogenation.

33. The method of claim 30, wherein a catalyst comprising Ni, Cu, Ru, Cr or a mixture thereof on a neutral support is used for the hydrogenation.

34. The method of claim 33, wherein a nickel-containing catalyst on an $\alpha$-$Al_2O_3$ support is used.

35. The method of claim 16, wherein the hydrogenation is carried out as a liquid-phase hydrogenation at a temperature of from 60 to 140° C. and a pressure of from 20 to 50 bar.

36. The method of claim 16, wherein the crude acetone contains up to 15% by weight of impurities.

37. The method of claim 16, wherein the acetone conversion in the hydrogenation is at least 99%.

* * * * *

UNITED STATES PATENT AND TRADEMARK OFFICE
CERTIFICATE OF CORRECTION

PATENT NO. : 6,841,704 B2
DATED : January 11, 2005
INVENTOR(S) : Michael Sakuth, Uwe Tanger and Markus Weber It is certified that error appears in the above-identified patent and that said Letters Patent is hereby corrected as shown below:

Title page,
Item [57], ABSTRACT,
Line 4, please delete "a" and insert therefore -- an --, and please delete "$SiO_2/Al_2O_3$" and insert therefore -- $SiO_2{:}Al_2O_3$ --.

Column 14,
Line 42, please delete "a" and insert therefore -- an --, and please delete "$SiO_2/Al_2O_3$" and insert therefore -- $SiO_2{:}Al_2O_3$ --.

Column 15,
Line 1, please delete "any".
Line 18, please delete "a" and insert therefore -- an --, and please delete "$SiO_2/Al_2O_3$" and insert therefore -- $SiO_2{:}Al_2O_3$ --.

Column 16,
Line 16, please delete "n-propylbenxene" and insert therefore -- n-propylbenzene --.
Line 19, please delete "7.5% weight" and insert therefore -- 7.5% by weight --.

Signed and Sealed this

Twenty-fourth Day of May, 2005

JON W. DUDAS
*Director of the United States Patent and Trademark Office*